United States Patent [19]

Schneider et al.

[11] Patent Number: 6,005,141
[45] Date of Patent: *Dec. 21, 1999

[54] USE OF GLYCINE-N,N-DIACETIC ACID DERIVATIVES AS BIODEGRADABLE COMPLEXING AGENTS FOR ALKALINE EARTH METAL IONS AND HEAVY METAL IONS AND PROCESS FOR THE PREPARATION THEREOF

[75] Inventors: Juergen Schneider, Freinsheim; Birgit Potthoff-Karl, Ludwigshafen; Alexander Kud, Eppelsheim; Richard Baur, Mutterstadt; Alfred Oftring, Bad Duerkheim; Thomas Greindl, Neuburg, all of Germany

[73] Assignee: BASF Aktiengesellschaft, Ludwigshafen, Germany

[ * ] Notice: This patent is subject to a terminal disclaimer.

[21] Appl. No.: 09/073,243

[22] Filed: May 6, 1998

Related U.S. Application Data

[62] Division of application No. 08/545,768, filed as application No. PCT/EP94/01838, Jun. 7, 1994, Pat. No. 5,786,313.

[30] Foreign Application Priority Data

Jun. 16, 1993 [DE] Germany .............................. 43 19 935

[51] Int. Cl.$^6$ ................................................. C07C 229/00
[52] U.S. Cl. ........................... 562/571; 562/565; 562/572
[58] Field of Search .................................. 562/571, 572, 562/565

[56] References Cited

U.S. PATENT DOCUMENTS

| | | | |
|---|---|---|---|
| 2,500,019 | 3/1950 | Bersworth | 562/608 |
| 3,668,246 | 6/1972 | Berding et al. | 562/572 |
| 3,733,355 | 5/1973 | Harris et al. | 562/572 |
| 3,961,932 | 6/1976 | Miller | 71/1 |
| 3,969,257 | 7/1976 | Murray | 510/376 |
| 4,001,133 | 1/1977 | Sorgenfrei et al. | 134/254 |
| 4,066,517 | 1/1978 | Stevens et al. | 205/265 |
| 4,287,080 | 9/1981 | Siklosi | 510/235 |
| 4,752,354 | 6/1988 | Beurich et al. | 162/72 |
| 4,806,263 | 2/1989 | Leathers et al. | 510/199 |
| 4,880,725 | 11/1989 | Hirai et al. | 430/373 |
| 4,973,730 | 11/1990 | Bauer et al. | 558/372 |
| 5,019,296 | 5/1991 | Bauer et al. | 510/480 |
| 5,177,243 | 1/1993 | Parker | 558/442 |
| 5,481,018 | 1/1996 | Athey et al. | 558/442 |
| 5,580,705 | 12/1996 | Ueda et al. | 430/400 |
| 5,849,950 | 12/1998 | Greindl et al. | 562/571 |

FOREIGN PATENT DOCUMENTS

| | | |
|---|---|---|
| 0 089 136 | 9/1983 | European Pat. Off. . |
| 2 027 972 | 4/1971 | Germany . |
| 4 211 713 | 10/1993 | Germany . |
| 55-157695 | 12/1980 | Japan . |
| 55-160099 | 12/1980 | Japan . |
| 1 283 635 | 8/1972 | United Kingdom . |
| 2 178 754 | 2/1987 | United Kingdom . |

OTHER PUBLICATIONS

Chemical Abstract No. 54:18377d (1960) Month Unknown.
Chemical Abstracts, No. 5, vol. 58, Mar. 4, 1963.
Chemical Abstracts, No. 18, vol. 95, Nov. 2, 1981.
Chemical Abstracts, No. 5, vol. 63, Aug. 30, 1965.
Chemical Abstracts, No. 14, vol. 103, Oct. 7, 1985.
Chemical Abstracts, No. 18, vol. 106, May 4, 1987.
Chemical Abstracts, 58, 4644e(1963).
Chemical Abstracts, 95, 9123m, 9124n(1981).

*Primary Examiner*—Gary Geist
*Assistant Examiner*—Taylor Victor Oh
*Attorney, Agent, or Firm*—Oblon, Spivak, McClelland, Maier & Neustadt, P.C.

[57] ABSTRACT

Glycine-N,N-diacetic acid derivatives and their alkali metal, alkaline earth metal, ammonium and substituted ammonium salts are used as complexing agents for alkaline earth metal and heavy metal ions with the exception of α-alanine-N,N-diacetic acid as textile detergent builders in powder detergent formulations and as calcium sequestrants in oral hygiene products.

4 Claims, No Drawings

USE OF GLYCINE-N,N-DIACETIC ACID DERIVATIVES AS BIODEGRADABLE COMPLEXING AGENTS FOR ALKALINE EARTH METAL IONS AND HEAVY METAL IONS AND PROCESS FOR THE PREPARATION THEREOF

This application is a division of U.S. Pat. No. 5,786,313, which is a 371 of PCT/EP94/01838.

The use of glycine-N,N-diacetic acid derivatives as biodegradable complexing agents for alkaline earth metal ions and heavy metal ions and process for the preparation thereof The present invention relates to the use of glycine-N,N-diacetic acid derivatives and their alkali metal, alkaline earth metal, ammonium and substituted ammonium salts as complexing agents for alkaline earth metal ions and heavy metal ions with the exception of α-alanine-N,N-diacetic acid as textile detergent builders in powder detergent formulations and as calcium sequestrants in oral hygiene products.

The present invention furthermore relates to a process for preparing glycine-N,N-diacetic acid derivatives and to intermediates arising in this process.

Since some of the glycine-N,N-diacetic acid derivatives represent novel substances, the invention also relates to these novel substances.

Japanese Published Specifications 80/157 695 (1) and 80/160 099 (2), quoted in Chem. Abstr. 95 (1981) 9123 m and 9124 n, respectively, disclose the use of alanine-N,N-diacetic acid in the form of the sodium salt as builder in textile detergents formulated in powder form, with an enhancement of the wash efficiency being observed in particular for cotton textiles.

EP-A 089 136 (3) relates to oral hygiene products which contain as calcium sequestrant inter alia a-alanine-N,N-diacetic acid. These are used to control the amount of calcium fluoride supplied to the dental enamel to protect from caries.

Complexing agents for alkaline earth metal ions and heavy metal ions used in a wide variety of industrial areas with their ranges of requirements and problems which in some cases differ greatly from one another are still normally systems which have been known and used for a long time such as polyphosphates, nitrilotriacetic acid or ethylenediaminetetraacetic acid. However, these agents show certain disadvantages, and the main weak points are, in particular, their calcium- and manganese-binding capacities which are still in need of improvement, their as yet non-optimal stabilizing action in bleaching baths and bleaching systems, and their biodegradability and ability to be eliminated, which are usually inadequate.

It was therefore an object of the present invention to provide complexing agents which no longer have the disadvantages of the prior art.

Accordingly, the use of glycine-N,N-diacetic acid derivatives of the general formula I

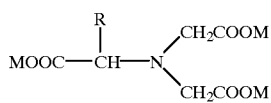

(I)

in which

R is $C_1$- to $C_{30}$-alkyl or $C_2$- to $C_{30}$-alkenyl, which can additionally carry as substituents up to 5 hydroxyl groups, formyl groups, $C_1$- to C4-alkoxy groups, phenoxy groups or $C_1$- to $C_4$-alkoxycarbonyl groups and be interrupted by up to 5 non-adjacent oxygen atoms, alkoxylate groups of the formula —$(CH_2)_k$—O—$(A^1O)_m$—$(A^2O)_n$—Y, in which $A^1$ and $A^2$ are, independently of one another, 1,2-alkylene groups with 2 to 4 carbon atoms, Y is hydrogen, $C_1$- to $C_{12}$-alkyl, phenyl or $C_1$- to $C_4$-alkoxycarbonyl, and k is the number 1, 2 or 3, and m and n are each numbers from 0 to 50, where the total of m+n must be at least 4, phenylalkyl groups with 1 to 20 carbon atoms in the alkyl, a five- or six-membered unsaturated or saturated heterocyclic ring with up to three heteroatoms from the group consisting of nitrogen, oxygen and sulfur, which can additionally be benzo-fused, carrying $C_1$- to $C_{20}$-alkyl groups, where all the phenyl nuclei and heterocyclic rings mentioned in the meanings of R can additionally also carry as substituents up to three $C_1$- to $C_4$-alkyl groups, hydroxyl groups, carboxyl groups, sulfo groups or $C_1$- to C4-alkoxycarbonyl groups, or a radical of the formula

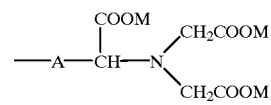

where A is a $C_1$- to $C_{12}$-alkylene bridge, preferably a $C_2$- to $C_{12}$-alkylene bridge, or a chemical bond, and M is hydrogen, alkali metal, alkaline earth metal-, ammonium or substituted ammonium in the appropriate stoichiometric amounts, as complexing agents for alkaline earth metal ions and heavy metal ions with the exception of a-alanine-N,N-diacetic acid as textile detergent builders in powder detergent formulations and as calcium sequestrants in oral hygiene products has been found.

In a preferred embodiment, the compounds I used are those in which R is $C_1$- to $C_{20}$-alkyl, $C_2$- to $C_{20}$-alkenyl or a radical of the formula

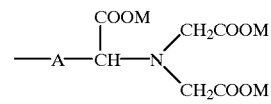

In a particularly preferred embodiment, the compound I used are α-alanine-N,N-diacetic acid (R=$CH_3$) and its alkali metal, ammonium and substituted ammonium salts.

Particularly suitable salts of this type are the sodium, potassium and ammonium salts, in particular the trisodium, tripotassium and triammonium salt, and organic triamine salts with a tertiary nitrogen atom.

Particularly suitable bases underlying the organic amine salts are tertiary amines such as trialkylamines with 1 to 4 carbon atoms in the alkyl, such as trimethyl- and triethylamine, and trialkanolamines with 2 or 3 carbon atoms in the alkanol residue, preferably triethanolamine, tri-n-propanolamine or triisopropanolamine.

The alkaline earth metal salts which are particularly used are the calcium and magnesium salts.

Besides methyl, particularly suitable as straight-chain or branched alk(en)yl radicals for the radical R are $C_2$- to $C_{17}$-alkyl and -alkenyl, and of these in particular straight-chain radicals derived from saturated or unsaturated fatty acids. Examples of specific R radicals are: ethyl, n-propyl, iso-propyl, n-butyl, iso-butyl, sec-butyl, tert-butyl, n-pentyl, iso-pentyl, tert-pentyl, neopentyl, n-hexyl, n-heptyl, 3-heptyl (derived from 2-ethylhexanoic acid), n-octyl, iso-octyl (derived from iso-non-anoic acid), n-nonyl, n-decyl, n-undecyl, n-dodecyl, iso-dodecyl (derived from iostridecanoic acid), n-tridecyl, n-tetradecyl, n-pentadecyl, n-hexadecyl, n-heptadecyl, n-octadecyl, n-nonadecyl, n-eicosyl and n-heptadecenyl (derived from oleic acid). Mixtures may also occur for R, in particular those derived from naturally occurring fatty acids and from synthetically produced industrial acids, for example by the oxo synthesis.

$C_1$- to $C_{12}$-Alkylene bridges A used are, in particular, polymethylene groups of the formula —$(CH_2)_k$-, in which k is a number from 2 to 12, in particular from 2 to 8, i.e. 1,2-ethylene, 1,3-propylene, 1,4-butylene, pentamethylene, hexamethylene, heptamethylene, octamethylene, nonamethylene, decamethylene, undecamethylene and dodecamethylene. Hexamethylene, octamethylene, 1,2-ethylene and 1,4-butylene are particularly preferred in this connection. However, it is also possible for branched $C_1$- to $C_{12}$-alkylene groups to occur besides, e.g. $CH_2CH(CH_3)CH_2$—, $CH_2C(CH_3)_2CH_2$—, —$CH_2CH(C_2H_5)$— or —$CH_2CH(CH_3)$—.

The $C_1$- to $C_{30}$-alkyl and $C_2$- to $C_{30}$-alkenyl groups can carry up to 5, in particular up to 3, additional substituents of the said type and be interrupted by up to 5, in particular up to 3, non-adjacent oxygen atoms. Examples of such substituted alk(en)yl groups are —$CH_2OH$, —$CH_2CH_2OH$, —$CH_2CH_2$—O—$CH_3$, —$CH_2CH_2$—O—$CH_2CH_2$O—$CH_3$, —$CH_2$—O—$CH_2CH_3$, —$CH_2$—O—$CH_2CH_2$—OH, —$CH_2$—CHO, —$CH_2$ OPh, —$CH_2$—$COOCH_3$ or —$CH_2CH_2$—$COOCH_3$.

Particularly suitable alkoxylate groups are those in which m and n are each numbers from 0 to 30, in particular from 0 to 15. $A^1$ and $A^2$ are groups derived from butylene oxide and, in particular, from propylene oxide and from ethylene oxide. Of particular interest are pure ethoxylates and pure propoxylates, but ethylene oxide/propylene oxide block structures can also occur.

Suitable five- or six-membered unsaturated or saturated heterocyclic rings with up to three heteroatoms from the group consisting of nitrogen, oxygen and sulfur, which can additionally be benzo-fused and substituted by the specified radicals, are:

tetrahydrofuran, furan, tetrahydrothiophene, thiophene, 2,5-dimethylthiophene, pyrrolidine, pyrroline, pyrrole, isoxazole, oxazole, thiazole, pyrazole, imidazoline, imidazole, 1,2,3-triazolidine, 1,2,3- and 1,2,4-triazole, 1,2,3-, 1,2,4- and 1,2,5-oxadiazole, tetrahydropyran, dihydropyran, 2H- and 4H-pyran, piperidine, 1,3- and 1,4-dioxane, morpholine, pyrazane, pyridine, α-, β- and γ-picoline, α- and γ-piperidone, pyrimidine, pyridazine, pyrazine, 1,2,5-oxathiazine, 1,3,5-, 1,2,3- and 1,2,4-triazine, benzofuran, thionaphthene, indoline, indole, isoindoline, benzoxazole, indazole, benzimidazole, chroman, isochroman, 2H- and 4H-chromene, quinoline, isoquinoline, 1,2,3,4-tetrahydroisoquinoline, cinnoline, quinazoline, quinoxaline, phthalazine and benzo-1,2,3-triazine.

N—H groups in the said heterocyclic rings should where possible be present in derivatized form, for example as N-alkyl group.

In the case of substitution on the phenyl nuclei or the heterocyclic rings there are preferably two (identical or different) or, in particular, a single substituent.

Examples of optionally substituted phenylalkyl groups and heterocyclic rings carrying alkyl groups for R are benzyl, 2-phenylethyl, 3-phenylpropyl, 4-phenylbutyl, o-, m- or p-hydroxybenzyl, o-, m- or p-carboxylbenzyl, o-, m- or p-sulfobenzyl, o-, m- or p-methoxy or -ethoxycarbonylbenzyl, 2-furylmethyl, N-methylpiperidin-4-ylmethyl or 2-, 3- or 4-pyridinylmethyl.

In the case of substitution on phenyl nuclei and on heterocyclic rings, preferably groups which confer solubility in water, such as hydroxyl groups, carboxyl groups or sulfo groups, occur.

Examples of the said $C_1$- to $C_4$-, $C_1$- to $C_{12}$- and $C_1$- to $C_{20}$-alkyl groups are also to be regarded as the corresponding radicals listed above for R.

A preferred use is in industrial cleaner formulations for hard surfaces made of metal, plastic, paint or glass.

Industrial cleaner formulations were sought for cleaning hard surfaces, in particular with improved properties in the removal of dirt. It is additionally desirable, to reduce waste water pollution, entirely to dispense with the organic solvents which are normally also used in such cases.

Particularly suitable areas of use are industrial cleaner formulations containing glycine-N,N-diacetic acid derivatives I or their salts are:

alkaline rust removers alkaline dip degreasers all-purpose cleaners car-wash compositions for brush and high-pressure washes steam jet cleaners electrolytic degreasers, especially for steel electrolytic rust removers electrolytic descalers highly alkaline cleaners high-pressure cleaners chain lubricants for the conveying belts of bottle filling and cleaning systems passivating agents for steel spray cleaners aqueous cold cleaners As a rule, these cleaner formulations contain 0.1 to 30% by weight of glycine-N,N-diacetic acid derivatives I or their salts.

Formulations customary for individual areas of use are known in principle to the skilled worker. As a rule, besides the complexing agents, such formulations contain 1 to 35 % by weight of surfactants which are anionic or, preferably, nonionic in nature and which are foaming or low-foam depending on the purposes of use, and, if required, as further aids further complexing agents, builders, foam suppressants, emulsifiers, corrosion inhibitors, reducing agents, solubilizers, dispersants and preservatives in the concentrations customary for this purpose. It is also possible for other components with a specific action to be included, depending on the purpose of use. It is substantially possible to dispense with organic solvents in the formulations described.

Suggested formulations for industrial cleaning formulations of these types are to be found, for example, in the technical information "Technische Reinigungsmittel" TI/ES 1167d of January 1991 of BASF Aktiengesellschaft; the prior art complexing agents indicated therein are to be replaced by glycine-N,N-diacetic acid derivatives I or their salts.

Another preferred use of glycine-N,N-diacetic acid derivatives I and their salts is in alkaline cleaner formulations for the beverage and foodstuff industries, in particular for bottle cleaning in the beverage industry and equipment cleaning in dairies, in breweries, in the canning, the baked goods, the sugar, the fat-processing and the meat-processing industries.

Formulations in particular with improved properties in removing dirt have been sought for cleaning containers and equipment in the beverage and foodstuffs industries. It is additionally desirable, in order to reduce waste water pollution, entirely to dispense with organic solvents in such formulations.

The present alkaline cleaner formulations have, as a rule, pH values from 8 to 14, preferably from 9 to 13, in particular from 10 to 12.

A preferred area of use of the described cleaner formulations is bottle cleaning in the beverage industry, in particular with automatic bottle-washing machines with throughputs of up to, normally, 30,000 to 70,000 bottles per hour. The dirty bottles contained, for example, beer, milk, soft drinks, fruit juices, unfermented wine or mineral water.

Another preferred area of use of the described cleaner formulations is the cleaning of equipment in dairies. They can be used with an advantageous effect in the cleaning of butter churns and workers, in which case what mainly matters is the removal of fat. Cleaners containing glycine-N,N-diacetic acid derivatives I or their salts are outstandingly suitable, however, in particular where it is needed to remove residues or deposits of calcium phosphate, other calcium salts, usually of organic acids, and casein, ("milk stone"), that is to say, for example, in milk plate heaters, disk packs for milk centrifuges or storage and transport tanks for milk.

Another preferred area of use of the described cleaner formulations is the cleaning of equipment in breweries. In this case, the need is, in particular, to remove residues or deposits of calcium oxalate, hop resins and protein compounds ("beer stone"), for example from fermentation tanks, storage tanks or beer pipes.

Another preferred area of use of the described cleaner formulations is the cleaning of equipment in the canning industry. When heating the tinplate cans which have been filled with foodstuffs and closed, normally in an autoclave, or in the final cleaning of cans, eg. in a continuous spray machine, it is necessary also to use cleaners which wash off the residues of the filling material without attacking the tinplate or its coating. In addition, the cleaner should prevent scale deposits settling on the cans or in the equipment.

Another preferred area of use of the described cleaner formulations is the cleaning of equipment in the baked goods industry, in particular the cleaning of baked and paste goods dies which are contaminated with burnt-on baking fat and dough residues. The cleaning normally takes place by boiling with the alkaline cleaning solutions or by washing in continuous spray systems.

Another preferred area of use of the described cleaner formulations is the cleaning of equipment in the sugar industry. Residues or contaminations containing calcium salts result in the production of sucrose from sugar beets or sugar cane, and the described formulations contain glycine-N,N-diacetic acid derivatives I or their salts are outstandingly suitable for removing them.

Another preferred area of use of the described cleaner formulations is the cleaning of equipment in the fat-processing industry which produces from fats of animal or vegetable origin in particular lard, tallow, edible oils or by catalytic hydrogenation hardened fats or fatty oils, eg. margarine. Products of this type represent, besides their importance in the foodstuffs sector, also important raw materials for producing products for textile finishing, paints, leather care compositions, cosmetic products, candles, soaps, surfactants, lubricants, plasticizers, cement and asphalt additives and plastics.

Another preferred area of use of the described cleaner formulations is the cleaning of equipment in the meat-processing industry. In this case it is necessary in particular to use cleaners which prevent scale, eg. in so-called steam jet cleaning equipment, in which a hot steam/liquid mixture impinges on the apparatus and equipment to be cleaned.

The described alkaline cleaner formulations containing glycine-N,N-diacetic acid derivatives I or their salts can be used substantially free of organic solvents. Possible environmental pollution is substantially precluded in this way.

An aqueous cleaner formulation customary for the listed areas of use in the beverage and foodstuffs industries contains (i) 0.05 to 30% by weight, preferably 0.1 to 25% by weight, in particular 0.5 to 15% by weight, of glycine-N,N-diacetic acid derivatives I or alkali metal, ammonium or substituted ammonium salts thereof, (ii) 2 to 50% by weight, preferably 5 to 40% by weight, in particular 8 to 25% by weight, of alkali metal hydroxide, carbonate, silicate or a mixture thereof and (iii) 1 to 30% by weight, preferably 2 to 25% by weight, in particular 3 to 20% by weight, of surfactants.

Suitable in this connection as component (ii) are, in particular, sodium and potassium hydroxides, but also sodium and potassium carbonates; it is also possible to use mixtures of said alkalies.

It is possible to use as surfactants (iii) all conventional anionic or nonionic surfactants or mixtures thereof, but alkyl sulfates, alkylsulfonates, fatty alcohol alkoxylates, oxo alcohol alkoxylates, alkyl polyglucosides and fatty amine alkoxylates are particularly suitable.

This composition represents a basic formulation for all stated areas of application. Specific composition differing from one another within this basic formulation are to be explained by the various types of foodstuff and beverage contaminations, the different amounts of alkaline earth metal ions in these residues and deposits and by the differences in the sensitivity of the materials in the containers and equipment to be cleaned in the various areas of application. It is also worth mentioning in this connection that the described alkaline cleaner formulations which contain glycine-N,N-diacetic acid derivatives I or their salts as a rule cause no corrosion, even on sensitive equipment materials.

The basic formulation of components (i) to (iii) described above can also contain conventional aids in the concentration customary in such cases, for example disinfectants to achieve the desired degree of bacteriological cleanliness, wetting agents, solubilizers, growth inhibitors or preservatives.

Another preferred use of glcyine-N,N-diacetic acid derivatives I and their salts is in dishwashing composition formulations, in particular in phosphate-free compositions for mechanical dishwashing in dishwashing machines in the household or in commercial operations, eg. large kitchens or restaurants.

Another preferred use of glycine-N,N-diacetic acid derivatives I and their salts is in bleaching baths in the paper industry. In this case, complexing agents are required in reductive bleaching, eg. with sodium dithionite, or in oxidative bleaching, eg. with hydrogen peroxide, in order to increase the efficiency of the bleaching process, ie. the degree of whiteness of the wooden ship. The complexing agents are thus used to eliminate heavy metal cations, mainly of iron, copper and, in particular, manganese, which also interfere with resin sizing with alum and sodium resinate owing to the formation of insoluble salts. The deposition of iron onto the paper leads to "hot spots" at which oxidative catalytic decomposition of the cellulose starts.

A typical formulation of an aqueous reductive bleaching bath of this type in the paper industry for ground wood pulp (for example 4% stock consistency) contains 0.05 to 0.1% by weight of complexing agent I and about 1% by weight of sodium dithionite, in each case based on the ground wood pulp. The bath temperature is about 60, the bleaching time is normally 1 hour and the pH is about 5.8.

A typical formulation of an aqueous oxidative bleaching bath of this type in the paper industry for ground wood pulp (for example 20% stock consistency) contains 0.05 to 0.15% by weight of complexing agent I, about 2% by weight of waterglass, about 0.75% by weight of NaOH and about 1% by weight of $H_2O_2$, in each case based on the ground wood pulp. The bath temperature is about 50° C. and bleaching time is normally 2 hours.

Another preferred use of glycine-N,N-diacetic acid derivatives I and their salts is in photographic bleaching and bleaching-fixing baths. These compounds can be used in such baths in the photographic industry which are made up with hard water in order to prevent the precipitation of sparingly soluble calcium and magnesium salts. The precipitates lead to gray fogs on films and pictures and deposits in the tanks, which can thus be advantageously avoided. They can advantageously be used as iron(III) complexing agent solutions in bleaching-fixing baths where they can replace the hexacyanoferrate solutions which are objectionable for ecological reasons.

A typical aqueous photographic bleaching or bleaching-fixing bath formulation of this type looks as follows:

| Iron(III) complex with complexing | | |
|---|---|---|
| agent I | 0.04 | to 0.4 mol/l |
| Free complexing agent I | | to 1.3 mol/l |
| Sodium thiosulfate | 0.2 | to 2.0 mol/l |
| Sodium sulfite | 0.2 | to 0.3 mol/l |

The pH of such a bath is normally 4 to 8.

Another preferred use of glycine-N,N-diacetic acid derivatives I and their salts is in pretreatment and bleaching baths in the textile industry. Pretreatment baths mean, in particular, desizing baths and alkaline pretreatment or mercerizing baths. These compounds can thus be used in the textile industry to remove traces of heavy metals during the production process for natural and synthetic fibers such as cotton, wool or polyester. In this way, many impairments such as dirt spots and streaks on the textiles, loss of brightness, poor wettability, unlevel dyeings and color faults are prevented.

A typical aqueous pretreatment bath of this type for textile manufacture contains:

0.1 to 10% by weight of the complexing agent I,
0.5 to 20% by weight of conventional wetting agents or emulsifiers,
0 to 10% by weight of a reducing agent such as sodium dithionite,
0 to 5% by weight of a buffer mixture to adjust a pH between 5 and 10 and further conventional aids such as preservatives or desizing agents, eg. enzymes such as amylase.

Another preferred use of glycine-N,N-diacetic acid derivatives I and their salts is in electroplating baths for sequestering contaminating heavy metal cations. In this case, they act as substitute for the highly toxic cyanides.

A typical composition of an aqueous electroplating bath of this type for the deposition of, for example, copper, nickel, zinc or gold which may be mentioned is the following copper bath:

| | |
|---|---|
| about 10 g/l | copper(II) sulfate pentahydrate |
| 10 to 12 g/l | formaldehyde |
| 12 to 15 g/l | complexing agent I |
| 1 to 2 g/l | of a $C_{13}/C_{15}$ oxo alcohol which has been reacted with 12 mol of ethylene oxide and 6 mol of propylene oxide, as wetting agent |

This bath is normally adjusted to pH 13 with sodium hydroxide solution; it may also contain conventional stabilizers such as amines or sodium cyanide.

As another preferred use, copper, iron, manganese and zinc complexes of the compounds I are used in plant feeding to eliminate heavy metal deficits. The heavy metals are given in this way as chelates in order to prevent precipitation as biologically inactive insoluble salts.

Glycine-N,N-diacetic acid derivatives I and their salts can in general be used in an advantageous manner wherever precipitates of calcium, magnesium and heavy metal salts interfere in industrial processes and are to be prevented, for example to prevent deposits and encrustations in boilers, pipelines, on spray nozzles or generally on smooth surfaces.

They can be used to stabilize phosphates in alkaline degreasing baths and prevent the precipitation of lime soaps and, in this way, prevent the "tarnishing" of non-ferrous surfaces and extend the useful lives of alkaline cleaner baths.

Cooling water treatment with the compounds I prevents deposits or redissolves those already present. One advantage is the general applicability in an alkaline medium and thus the elimination of corrosion problems.

They can be used to prepare the redox catalyst used in the polymerization of rubber. They additionally prevent the precipitation of iron hydroxide in the alkaline polymerization medium.

The compounds I can be used as complexing agent or as builder in powder detergent formulations for textile washing. A use of this type as builder has already been disclosed for a-alanine-N,N-di-acetic acid. Besides conventional formulations (bulk density about 450 g/l), in this connection compact and ultra-compact detergents (bulk density≧700 g/l) are becoming increasingly important. As is well known, compact detergent formulations have a higher content of detergent substance (surfactants), builders (eg. zeolites), bleaches and polymers than conventional powder detergents. The compounds I are normally effective in such compact detergent formulations in amounts of from 0.1 to 25% by weight, in particular 1 to 15% by weight.

In liquid detergent formulations for textile washing, the compounds I can be used as complexing agents in an amount of from 0.05 to 20% by weight based on the total weight of the detergent formulation.

In liquid detergent formulations, the compounds I can furthermore also be used as preservatives, expediently in an amount of from 0.05 to 1% by weight based on the total weight of the detergent formulation.

In soaps, they prevent metal-catalyzed oxidative decompositions.

Examples of further suitable applications are applications in pharmaceuticals, cosmetics and foodstuffs in order, for example, to prevent the metal-catalyzed oxidation of olefinic double bonds and thus the products becoming rancid.

Other areas of application of the compounds I are in flue gas scrubbing, in particular to remove $NO_x$ from flue gases, in $H_2S$ oxidation, in metal extraction and the application as catalysts for organic syntheses, eg. atmospheric oxidation of paraffins or hydroformulation of olefins to alcohols.

An advantageous effect of the glycine-N,N-diacetic acid derivatives I or their salts is in bleach stabilization, for example in the bleaching of textiles, cellulose or paper. Traces of heavy metals such as iron, copper and manganese occur in the components of the bleaching bath itself, in the water and in the material to be bleached and catalyze the decomposition of the bleach. The complexing agents I bind these metal ions and prevent unwanted decomposition of the bleaching system during storage and on use. In this way, the efficiency of the bleaching system is increased, and damage to the material to be bleached is diminished.

Another advantageous effect of the glycine-N,N-diacetic acid derivatives I or their salts is in the strong bleach-activating effect of complexes of compounds I with manganese, in particular manganese of oxidation state II and IV. Complexes of this type can be used as substitute for conventional bleach activators in textile detergent formulations as bleach catalysts in amounts in the ppm range.

Glycine-N,N-diacetic acid derivatives I and their salts are suitable for the described purposes of use in particular because they represent exceptionally efficient complexing agents for alkaline earth metal ions and for heavy metal ions, in particular for calcium and manganese. Their calcium- and their manganese-binding capacities are exceptionally high.

Further advantages are their very low toxicity potential and their good biodegradability. Thus, a-alanine-N,N-diacetic acid shows a biodegradability of >90% (28-day value) in the Zahn-Wellens test under standard conditions, whereas, for example, ethylenediaminetetraacetic acid yields a value of <10% under the same conditions.

In association with their good biodegradability, it is also very advantageous that the cleaner formulations containing the compounds I can mostly be used substantially free of organic solvents. This precludes possible environmental pollution even more substantially.

The present invention also relates to a process for preparing glycine-N,N-diacetic acid derivatives I and their alkali metal, alkaline earth metal, ammonium and substituted ammonium salts, which comprises reacting (A) appropriate 2-substituted glycines or 2-substituted glycinonitriles or doubled glycines of the formula

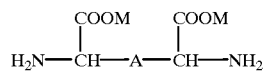

or doubled glycinonitriles of the formula

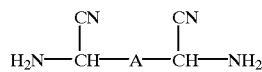

with formaldehyde and hydrogen cyanide or alkali metal cyanide or (B) iminodiacetic acid or iminodiacetonitrile with appropriate monoaldehydes or dialdehydes of the formula OHC—A—CHO and hydrogen cyanide or alkali metal cyanide and subsequently hydrolyzing nitrile groups which are still present to carboxyl group.

The two specified embodiments A and B represent examples of the "Strecker synthesis" in which, in general, aldehydes are reacted with ammonia or amines and hydrocyanic acid ("acidic" variant) or cyanides ("alikaline" variant) to give amino acids or derivatives thereof.

The "alkaline" variant of the Strecker synthesis is described in general form, for example, in U.S. Pat. No. 3,733,355 (4). However, the examples cited therein show that a high proportion of byproducts, especially of unwanted glycolic acid, always occurs; this can be concluded from the conversions of only a maximum of about 89%.

The "acidic" variant of the Strecker synthesis is disclosed, for example, in DE-A 20 27 972 (5). The preparation of carboxymethyliminodiacetonitrile starting from glycine, formaldehyde and hydrocyanic acid in an acidic medium is described therein. It is recommended in this case to add additional acid in order to keep the pH in the range below 7.

It was also an object of the present invention to provide a more efficient and more economic process for preparing glycine-N,N-di-acetic acid derivatives I, which, in particular, suppresses the formation of unwanted byproducts and is able to dispense with additional auxiliaries, for example for pH control.

The process defined above has accordingly been found.

The variants which make use of hydrogen cyanide ("acidic" variant) have proven particularly advantageous. It is expedient to use anhydrous hydrogen cyanide which is normally handled in this form on the industrial scale. In this connection, very particularly advantageous reactions are those starting from 2-substituted glycines or doubled glycines of the formula

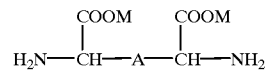

or from iminodiacetonitrile.

The reaction according to A or B is preferably carried out in water but also in an organic solvent or in mixtures thereof. Organic solvents which are preferably used are those which are partly or completely miscible with water, eg. methanol, ethanol, n-propanol, iso-propanol, tert-butanol, dioxane or tetrahydrofuran. It is also possible to use solubilizers.

In embodiment A it is expedient to use per mole of amino compound 2 to 2.6 mol of formaldehyde, preferably in the form of its aqueous approximately 30% by weight solution, or 2 to 2.6 mol of aldehyde, in anhydrous form or as aqueous solution, and 2 to 2.3 mol of hydrogen cyanide or alkali metal cyanide, for example sodium or potassium cyanide. The reaction is normally carried out at temperatures from 0 to 120° C., in particular 15 to 80° C., in the case of anhydrous hydrogen cyanide, and at 40 to 110° C., in particular 70 to 100° C., in the case of alkali metal cyanides. A suitable pH range for the reaction with anhydrous hydrogen cyanide when mineral acids such as sulfuric, hydrochloric or orthophosphoric acid are also used in embodiment B is, as a rule, from 0 to 11, in particular from 1 to 9, and the reaction with alkali metal cyanides is normally carried out at pH 10 to 14, in particular 11 to 13.

This reaction is followed by a hydrolysis of nitrile groups which are still present to carboxyl groups, which is carried out in a manner known per se in aqueous reaction medium in the presence of bases such as sodium or potassium hydroxide solution or of acids such as sulfuric or hydrochloric acid at temperatures from 20 to 110° C., in particular 40 to 100° C.

The glycine and glycinonitrile derivatives used as starting amino compounds can be used both as racemates and as enantiomerically pure D or L compounds.

According to the reaction conditions, the glycine-N,N-diacetic acid derivatives I are obtained as free carboxylic acid or, for example, as alkali metal salt. The required salts can be prepared without difficulty from the free acid by neutralization with the appropriate bases, for example amine bases.

The glycine-N,N-diacetic acid derivatives I and their salts can be isolated in pure form from their solutions without difficulty. Suitable for this purpose are, in particular, spray or freeze drying, crystallization and precipitation. It may be advantageous for the solution produced in the preparation to be supplied directly for industrial use.

The present invention also relates to the glycine-N,N-diacetonitriles and glycinonitrile-N,N-diacetonitriles which have not yet been disclosed in the literature and are substituted by the radical R in position 2, in which R is $C_1$- to $C_{30}$-alkyl or $C_2$- to $C_{30}$-alkenyl which can additionally carry as substituents up to 5 hydroxyl groups, formyl groups, $C_1$- to $C_4$-alkoxy groups, phenoxy groups or $C_1$- to $C_4$-alkoxycarbonyl groups and be interrupted by up to 5 non-adjacent oxygen atoms, alkoxylate groups of the formula $-(CH_2)_k-O-(A^1O)_m-(A^2O)_n-Y$, in which $A^1$ and $A^2$ are, independently of one another, 1,2-alkylene groups with 2 to 4 carbon atoms, Y is hydrogen, $C_1$- to $C_{12}$-alkyl, phenyl or $C_1$- to $C_4$-alkoxycarbonyl, and k is the number 1, 2 or 3, and m and n are each numbers from 0 to 50, where the total of m+n must be at least 4, phenylalkyl groups with 1 to 20 carbon atoms in the alkyl, a five- or six-membered unsaturated or saturated heterocyclic ring with up to three heteroatoms from the group consisting of nitrogen, oxygen and sulfur, which can additionally be benzo-fused, carrying $C_1$- to $C_{20}$-alkyl groups, where all phenyl nuclei and heterocyclic rings mentioned in the meanings for R can additionally carry as substituents up to three $C_1$- to $C_4$-alkyl groups, hydroxyl groups, carboxyl groups, sulfo groups or $C_1$- to $C_4$-alkoxycarbonyl groups, for example the compounds α-alanine-N,N-diacetonitrile and α-alaninonitrile-N,N-diacetonitrile, and doubled glycine-N,N-diacetonitriles and doubled glycinonitrile-N,N-diacetonitriles of the formula

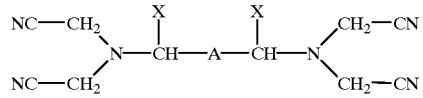

where X is a carboxylic acid or a nitrile functionality, as intermediates for the preparation of glycine-N,N-diacetic acid derivatives I and their salts. These compounds arise as intermediates in the reaction of said glycine and glycinonitrile derivatives for formaldehyde and hydrogen cyanide or of iminodiacetonitrile with the appropriate mono- or dialdehydes and hydrogen cyanide.

In the process according to the invention it is possible with the "acidic" variant of embodiment A with glycines substituted in position 2 or doubled glycines of the formula

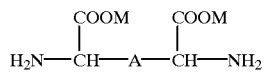

as starting material to dispense with additional acid because, astonishingly, the acidity of the carboxyl group which is present is sufficient to carry out the reaction.

The reaction product is generally obtained in high yield in sufficiently pure form. The content of byproducts is low. Further advantages of the preparation process according to the invention are the salt-free procedure and the easily available starting materials.

The present invention also relates to the glycine-N,N-diacetic acid derivatives of the general formula Ia

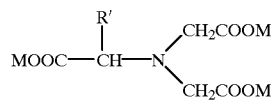

which have not yet been described in the literature, and in which

R' is $C_4$–$C_{30}$-alkyl, in particular $C_5$–$C_{30}$-alkyl, or $C_2$–$C_{30}$-alkenyl, which can additionally carry as substituents up to 5 hydroxyl groups, formyl groups, $C_1$- to $C_4$-alkoxy groups, phenoxy groups or $C_1$- to $C_4$-alkoxycarbonyl groups and be interrupted by up to 5 non-adjacent oxygen atoms, alkoxylate groups of the formula $-(CH_2)_k-O-(A^1O)_m-(A^2O)_n-Y$, in which $A^1$ and $A^2$ are, independently of one another, 1,2-alkylene groups with 2 to 4 carbon atoms, Y is hydrogen, $C_1$- to $C_{12}$-alkyl, phenyl or $C_1$- to $C_4$-alkoxycarbonyl, and k is the number 1, 2 or 3, and m and n are each numbers from 0 to 50, where the total of m+n must be at least 4, phenylalkyl groups with 1 to 20 carbon atoms in the alkyl, a five- or six-membered unsaturated or saturated heterocyclic ring with up to three heteroatoms from the group consisting of nitrogen, oxygen and sulfur, which can additionally be benzo-fused, carrying $C_1$- to $C_{20}$-alkyl groups, where all phenyl nuclei and heterocyclic rings mentioned in the meanings for R can additionally carry as substituents up to three $C_1$- to $C_4$-alkyl groups, hydroxyl groups, carboxyl groups, sulfo groups or $C_1$- to $C_4$-alkoxycarbonyl groups, or a radical of the formula

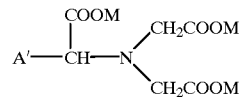

where A' is a $C_1$- to $C_{12}$-alkylene bridge, and

M is hydrogen, alkali metal, alkaline earth metal, ammonium or substituted ammonium in the appropriate stoichiometric amounts.

The compounds I with R=$C_1$- to $C_3$-alkyl have already been disclosed in the reference Chem. zvesti 28(3), 332–335 (1974).

PREPARATION EXAMPLES

Example 1

Preparation of α-D,L-alanine-N,N-diacetic trisodium salt from iminodiacetonitrile 14 g of sulfuric acid (100% by weight), 27 g of anhydrous hydrocyanic acid and 44 g of acetaldehyde (100% by weight) were successively added to a suspension of 95 g of iminodiacetonitrile (100% by weight) in 500 ml of water at 35 to 50° C. The mixture was stirred until no further change was found on titration of the hydrocyanic acid content. After cooling to 10° C., the precipitate was filtered off and dried. 123.4 g of α-D,L-alaninonitrile-N,N-diacetonitrile (corresponding to 83% of theory) of melting point 82° C. resulted.

The resulting α-D,L-alaninonitrile-N,N-diacetonitrile was introduced at 50° C. into 440 g of 25% by weight aqueous sodium hydroxide solution, and the mixture was then stirred at this temperature for a further 2 hours. It was then heated at 95° C. for 10 hours. Towards the end of the reaction, the reaction mixture was diluted with water. This resulted in 610 g of an aqueous solution of α-D,L-alanine-N,N-diacetic acid trisodium salt with an iron-binding capacity of 1.285 mmol/g (corresponding to 94% of theory based on α-D,L-alaninonitrile-N,N-diacetonitrile used).

Example 2

Preparation of α-D,L-alanine-N,N-diacetic acid trisodium salt from α-D,L-alanine 105 g of formaldehyde (30% by weight) and 31.7 g of hydrocyanic acid (89.5% by weight) were added simultaneously to a suspension of 44 g of D,L-alanine (>99% by weight) in 200 g of water at 30° C. The mixture was then stirred at 30° C. for 3 hours. The decrease in hydrocyanic acid corresponded to a conversion of >97% of theory.

The aqueous solution of α-D,L-alanine-N,N-diacetonitrile obtained in this way was added dropwise to 132 g of 50% by weight sodium hydroxide solution at 30° C. After stirring at 30° C. for 8 hours, the temperature was raised to 95 to 102° C. After a further 4 hours, the reaction was virtually complete. 352.5 g of a solution which, according to its iron-binding capacity, contained 37.4% by weight of α-D,L-alanine-N,N-diacetic acid trisodium salt were obtained (corresponding to a yield of 97.4% of theory over the two stages).

Example 3

L-Tyrosine-N,N-diacetic acid trisodium salt from L-tyrosine 45.8 g of tyrosine were suspended in 200 ml of water, and 7.5 g of HCN (90% by weight) and 25 g of formaldehyde (30% by weight) in aqueous solution were added. After 2.5 h at 40° C., the conversion of hydrocyanic acid was a maximum, and a further 12.0 g of HCN (90% by weight) and 40.0 g of formaldehyde (30% by weight) in aqueous solution were added at pH 1. After a further 5 h at 35° C. and 4 h at 80° C., a solution of L-tyrosine-N,N-diacetonitrile was obtained in 94% yield of theory.

This solution was added dropwise to 130 g of 50% by weight aqueous sodium hydroxide solution at 40° C. After 2 h at 60° C. and 2 h at 95° C., 385 g of a solution of L-tyrosine-N,N-diacetic acid trisodium salt with an iron-binding capacity of 0.543 mmol/g (corresponding to 89% of the theoretical yield) were obtained.

Example 4

D,L-Ethylglycine-N,N-diacetic acid trisodium salt from iminodiacetonitrile 41 g of sulfuric acid (96% by weight), 180 g of hydrogen cyanide (99% by weight) and 385 g of propionaldehyde (99.5% by weight) were successively added dropwise to a suspension of 570 g of iminodiacetonitrile in 2070 g of water, and the mixture was stirred at 35° C. until no further change in the hydrocyanic acid content was detectable by titration. After cooling to 10° C., 977 g (97% yield of theory) of D,L-ethylglycinonitrile-N,N-diacetonitrile were obtained as precipitate by filtration with a purity of 96.8% by weight.

The precipitate was then introduced into 4430 g of a 17% by weight aqueous sodium hydroxide solution at 60° C. and then stirred at 60° C. for 3 h and at 95° C. for 10 h, and finally diluted with water. This resulted in 5275 g of a solution of D,L-ethylglycone-N,N-diacetic acid trisodium salt with an iron-binding capacity of 0.985 mmol/g (corresponding to 89% yield of theory).

Example 5

D,L-Propylglycine-N,N-diacetic acid trisodium salt from iminodiacetonitrile 14 g of sulfuric acid (96% by weight), 26.9 g of hydrogen cyanide (99.3%) and 79.3 g of butyraldehyde were successively added dropwise to a suspension of 95 g of iminodiacetonitrile in 550 g of water, and the mixture was stirred at 35° C. for 4 h until no further change in the hydrocyanic acid content was detectable by titration. After cooling to 10° C., 165 g (94% yield of theory) of D,L-n-propylglycinonitrile-N,N-diacetonitrile were obtained by phase separation.

70.4 g of this oil were then introduced into 350 g of a 15% by weight aqueous sodium hydroxide solution at 40° C., and the mixture was then stirred at 95° C. for 2 h and subsequently diluted with water. This resulted in 600 g of a solution of D,L-n-propylglycine-N,N-diacetic acid trisodium salt with an iron-binding capacity of 0.573 mmol/g (corresponding to 86% yield of theory).

Example 6

D,L-1-Methylpropylglycine-N,N-diacetic acid trisodium salt from iminodiacetonitrile 6 g of sulfuric acid (96% by weight), 30 g of hydrogen cyanide (99.4% by weight) and 103.2 g of 2-methylbutyraldehyde were successively added dropwise to a suspension of 95 g of iminodiacetonitrile in 350 g of water, and the mixture was stirred at 35° C. for 2 h and at 55° C. for 25 h until no further change in the hydrocyanic acid content was detectable by titration. After cooling to 10° C., 167 g (88% yield of theory) of D,L-1-methylpropylglycinonitrile-N,N-diacetonitrile were obtained by phase separation.

143 g of this oil were then introduced into 600 g of an 18% by weight aqueous sodium hydroxide solution at 40° C. and this was then stirred at 95° h for 20 h and subsequently diluted with water. This resulted in 960 g of a solution of D,L-1-methylpropylglycine-N,N-diacetic acid trisodium salt with an iron-binding capacity of 0.619 mmol/g (corresponding to 79% yield of theory).

Example 7

D,L-2-Methylpropylglycine-N,N-diacetic acid trisodium salt from iminodiacetonitrile 7 g of sulfuric acid (96% by weight), 30 g of hydrogen cyanide (98.3% by weight) and 103.4 g of 3-methylbutyraldehyde were successively added dropwise to a suspension of 95 g of aminodiacetonitrile in 350 g of water, and the mixture was stirred at 35° C. for 2 h and at 50° C. for 3 h until no further change in the hydrocyanic acid content was detectable by titration. After cooling to 10° C., 175 g (92% yield of theory) of D,L-2-methylpropylglycinonitrile-N,N-diacetonitrile were obtained by phase separation.

The resulting oil was then introduced into 860 g of a 14% by weight aqueous sodium hydroxide solution at 40° C. and then stirred at 60° C. for 3 h and at 95° C. for 5 h. This resulted in 1070 g of a solution of D,L-2-methylpropylglycine-N,N-diacetic acid trisodium salt with an iron-binding capacity of 0.775 mmol/g (corresponding to 90% yield of theory).

Example 8

D,L-n-Nonylglycine-N,N-diacetic acid from iminodiacetonitrile 14 g of sulfuric acid (96% by weight), 30.2 g of hydrogen cyanide (98.4% by weight) and 172 g of n-decanal were successively added dropwise to a suspension of 95 g of iminodiacetonitrile in 500 g of water, and the mixture was stirred at 60° C. for 17 h and at 80° C. for 2 h until no further change in the hydrocyanic acid content was detectable by titration. After cooling to 10° C., the aqueous phase was separated off and the remaining oil was extracted by shaking twice with 500 ml of water, and 205 g (79% yield of theory) of D,L-n-nonylglycinonitrile-N,N-diacetonitrile were obtained from the organic phase.

205 g of this oil were then introduced into 600 g of an 18% by weight aqueous sodium hydroxide solution together with 600 ml of n-butanol at 40° C. and the mixture was stirred at 95° C. for 30 h. The volatiles were then removed by distillation, and the residue was taken up in water, adjusted to pH 1 with HCl, and the precipitate which formed was isolated by filtration. This resulted in 209 g of D,L-n-nonylglycine-N,N-diacetic acid with an iron-binding capacity of 2.57 mmol/g (corresponding to 68% yield of theory).

Example 9

D,L-n-Tridecylglycine-N,N-diacetic acid from iminodiacetonitrile 14 g of sulfuric acid (96% by weight), 30.2 g of hydrogen cyanide (98.4% by weight) and 234 g of n-tetradecanal were successively added dropwise to a suspension of 95 g of iminodiacetonitrile in 500 g of water, and the mixture was stirred at 60° C. for 17 h and at 80° C. for 2 h until no further change in the hydrocyanic acid content was detectable by titration. After cooling to 10° C., the aqueous phase was separated off and the remaining oil was extracted by shaking twice with 500 ml of water, and 259 g (82% yield of theory) of D,L-n-tridecylglycinonitrile-N,N-diacetonitrile were obtained from the organic phase.

259 g of this oil were then introduced into 600 g of an 18% by weight aqueous sodium hydroxide solution together with 600 ml of n-butanol at 40° C. and the mixture was stirred at 95° C. for 30 h. The volatiles were then removed by distillation, and the residue was taken up in water, adjusted to pH 1 with HCl, and the wax-like precipitate which formed was isolated by filtration. This resulted in 252 g of D,L-n-tetradecylglycine-N,N-diacetic acid with an iron-binding capacity of 2.14 mmol/g (corresponding to 66% yield of theory).

Example 10

D,L-(2-Phenylethylene)glycine-N,N-diacetic acid trisodium salt from iminodiacetonitrile 3.5 g of sulfuric acid (96 % by weight), 8.0 g of hydrogen cyanide (98.3% by weight) and 35.2 g of 3-phenylpropionaldehyde were successively added dropwise to a suspension of 23.8 g of iminodiacetonitrile in 125 g of methanol, and the mixture was stirred at 50° C. for 50 h, after which time the conversion according to the hydrocyanic acid content was 95.5 % of theory.

Then 190 g of the untreated solution of D,L-(2-phenylethylene)-glycinonitrile-N,N-diacetonitrile in methanol were introduced into 186 g of a 19% by weight aqueous sodium hydroxide solution at 40° C., and the mixture was stirred at 60° C. for 3 h and at 95° C. for a further 22 h, with the methanol which distilled out being replaced by water. This resulted in 510 g of a solution of D,L-(2-phenylethylene)glycine-N,N-diacetic acid trisodium salt with an iron-binding capacity of 0.368 mmol/g (corresponding to 75% yield of theory). Acidification to pH 1.5, filtration of the precipitate which formed with suction and washing with methanol at 40° C. resulted in the corresponding free acid in a purity of 96% by weight.

Example 11

2-Furylmethyleneglycine-N,N-diacetic acid from iminodiacetonitrile 4.8 g of sulfuric acid (96% by weight), 16.5 g of hydrogen cyanide (90.2% by weight) and 52.9 g of furfural were successively added dropwise to a suspension of 47.5 g of iminoacetonitrile in 200 g of water, and the mixture was stirred at 60° C. for 6 h and at 85° C. for 8 h until no further change in the hydrocyanic acid content was detectable by titration. The mixture was saturated with sodium chloride and extracted three times by shaking with methyl tert-butyl ether. The combined organic phases were cooled to 20° C., and the precipitate which formed was isolated. 95 g (89% yield of theory) of D,L-2-furylmethyleneglycinonitrile-N,N-diacetonitrile resulted.

46 g of these crystals were then introduced into 130 g of a 22% by weight aqueous sodium hydroxide solution at 40° C., and the mixture was stirred at 40° C. for 3 h and at 95° C. for 4 h. It was subsequently adjusted to pH 1.5 with HCl, and the precipitate which formed was isolated by filtration and washed with water. This resulted in 47 g of D,L-2-furylmethyleneglycine-N,N-diacetic acid with an iron-binding capacity of 3.61 mmol/g (corresponding to 79% yield of theory).

Example 12

1,3-Propylenebis(D,L-glycine-N,N-diacetic acid) hexasodium salt from iminodiacetonitrile 14 g of sulfuric acid (96% by weight), 33.1 g of hydrogen cyanide (89.8% by weight) and 220 g of glutaraldehyde (25% by weight in water) were successively added dropwise to a suspension of 95 g of iminodiacetonitrile in 410 g of water, and the mixture was stirred at 35° C. for 2 h and at 70° C. for 6 h until no further change in the hydrocyanic acid content was detectable by titration (99.1% conversion of theory). After cooling to 10° C., the aqueous phase was separated off and the remaining oil was extracted by shaking twice with 500 ml of water, and 149 g (97% yield of theory) of 1,2-propylenebis(D,L-glycinonitrile-N,N-diacetonitrile) were obtained from the organic phase.

Then 149 g of this oil were introduced into 744 g of a 19% by weight aqueous sodium hydroxide solution at 30° C., and the mixture was stirred at 70° C. for 12 h and at 100° C. for 11 h. 572 g of a solution of 1,3-propylenebis(D,L-glycine-N,N-diacetic acid) hexasodium salt with an iron-binding capacity of 0.829 mmol/g (corresponding to 99% of the theoretical yield) were obtained. The product was isolated pure by adding methanol to the solution.

Technical application data and application examples

Determination of the calcium-binding capacity

Principle of the measurement

The inhibiting effect of complexing agents or dispersants on the precipitation of calcium carbonate is determined by turbidity titration. The substance to be investigated is introduced and titrated in the presence of sodium carbonate with calcium acetate solution. The endpoint is indicated by formation of the calcium carbonate precipitate. Use of a sufficient amount of sodium carbonate ensures that the measurement provides a correct result even if the effect derives not only from complexation of the calcium ions but from dispersion of calcium carbonate. This is so because if the amounts of sodium carbonate used are too small there is a risk that the dispersing capacity of the product will not be exhausted; in this case, the titration endpoint is determined by precipitation of the calcium salt of the compound investigated.

During the titration, the change in the light transmission is followed with the aid of a light-guide photometer. In the latter, a light beam guided via a glass fiber into the solution is reflected at a mirror, and the intensity of the reflected light is measured.

Reagents 0.25 M $Ca(OAc)_2$ solution

10% by weight $Na_2CO_3$ solution

1N NaOH solution

1% by weight hydrochloric acid

Procedure 1 g of active substance (A.S.) in the form of the trisodium salt is dissolved in 100 ml of distilled $H_2O$. Subsequently 10 ml of 10% by weight $Na_2CO_3$ solution are added. Automatic titration is carried out with 0.25 M $Ca(OAc)_2$ solution continuously at 0.25 ml/min and at room temperature (RT) with a pH of 11 kept constant during the titration and at 80° C. with a pH of 10.

Calculation

Amount in mg of $CaCO_3$/g of A.S.=ml of $Ca(OAc)_2$ solution used x 25. In the automatic titration, the 1st break point in the titration plot is the endpoint.

Furthermore, the perborate stabilization of the cleaner formulations 1 and 2 of the compositions indicated below was determined The hydrogen peroxide which is responsible for the bleaching action in detergent formulations containing sodium perborate is catalytically decomposed by heavy metal ions (Fe, Cu, Mn). This can be prevented by complexing the heavy metal ions. The peroxide-stabilizing effect of the complexing agents is tested via the remaining peroxide content after storage of a wash liquor containing heavy metals in the warm. The hydrogen peroxide content was determined before and after the storage by titration with potassium ermanganate in acidic solution.

Two detergent formulations are used to test for perborate stabilization, the decomposition taking place on storage in the warm by adding heavy metal catalysts (2.5 ppm mixture of 2 ppm $Fe^{3+}$, 0.25 ppm $Cu^{2+}$, 0.25 ppm $Mn^{2+}$).

1. Phosphate-containing formulation

| Composition (in % by weight) | |
|---|---|
| 19.3% | sodium $C_{12}$-alkylbenzenesulfonate (50% by weight aqueous solution) |
| 15.4% | sodium perborate·4 $H_2O$ |
| 30.8% | sodium triphosphate |
| 2.6% | copolymer of maleic acid and acrylic acid (50:50 ratio by weight, average molecular weight 50,000) |
| 31.0% | sodium sulfate, anhydrous |
| 0.9% | complexing agent according to the invention or comparative compound |

The detergent concentration was 6.5 g/l using water of 25° German hardness. Storage took place at 80° C. for 2 hours.

2. Reduced phosphate formulation

| Composition (in % by weight) | |
|---|---|
| 15% | sodium $C_{12}$-alkylbenzenesulfonate (50% by weight aqueous solution) |
| 5% | adduct of 11 mol of ethylene oxide and 1 mol of tallow fatty alcohol |
| 20% | sodium perborate·4 $H_2O$ |
| 6% | sodium metasilicate·5 $H_2O$ |
| 1.25% | magnesium silicate |
| 20% | sodium triphosphate |
| 31.75% | sodium sulfate, anhydrous |
| 1% | complexing agent according to the invention or comparative compound |

The detergent concentration was 8 g/l using water with 25° German hardness. The storage took place at 60° C. for 1 hour.

The following Table 1 shows the results of the determinations.

TABLE 1

| | Calcium carbonate dispersing capacity mg | | | | Perborate stabilization | |
|---|---|---|---|---|---|---|
| | $CaCO_3$/g A.S. | | $CaCO_3$/mol A.S. | | [%] | |
| | RT | 80° C. | RT | 80° C. | Formulation | |
| Complexing agent | pH 11 | pH 10 | pH 11 | pH 10 | 1 | 2 |
| α-ADA-Na₃ from Ex. No. 2 | 370 | 330 | 1.00 | 0.89 | 32.4 | 40.8 |
| for comparison: | | | | | | |
| Pentasodium triphosphate | 215 | 150 | 0.79 | 0.55 | — | — |
| NTA-Na₃ | 350 | 250 | 0.90 | 0.64 | 24.5 | 32.5 |
| EDTA-Na₄ | 275 | 240 | 1.04 | 0.91 | 20.0 | 34.0 |

α-ADA-Na₃ = α-Alanine-N,N-diacetic acid trisodium salt
NTA-Na₃ = Nitrilotriacetic acid trisodium salt
EDTA-Na₄ = Ethylenediaminetetraacetic acid tetrasodium salt Determination of the manganese-binding capacity Method of measurement 10.0 ml of 0.005 M $MnSO_4 \cdot H_2O$ solution are mixed with 50 ml of distilled water, 10 drops of 5% by weight potassium sodium tartrate solution, about 3 ml of a buffer solution, about 30 mg of ascorbic acid and a spatula tip of indicator (1 part by weight of Eriochrome black T ground with 400 parts by weight of NaCl) and heated to 75 C. The solution is titrated with a 0.001 M solution of the complexing agent (C.A.) until the change to blue persists.

Evaluation $$\text{mg Mn}^{2+}/\text{g C.A.} = \frac{274.7 \times 1000}{\text{ml used} \times \text{C.A. molecular weight}}$$

$$\text{mol Mn}^{2+}/\text{mol C.A.} = \frac{274.7 \times 1000}{\text{ml used} \times 54.94}$$

The following Table 2 shows the results of the determinations.

TABLE 2

| Complexing agent | mg $Mn^{2+}$/g complexing agent | mol $Mn^{2+}$/mol complexing agent |
|---|---|---|
| α-ADA-Na₃ from Ex. No. 2 | 209 | 0.86 |

TABLE 2-continued

| Complexing agent | mg Mn²⁺/g complexing agent | mol Mn²⁺/mol complexing agent |
|---|---|---|
| for comparison: EDTA-Na₄ | 192 | 1.02 |

Highly alkaline cleaner formulation for dairies
A mixture of 40 parts by weight of 50% by weight sodium hydroxide solution, 20 parts by weight of a 30 % by weight aqueous solution of α-D,L-alanine-N,N-diacetic acid trisodium salt from Example No. 2, 4 parts by weight of a $C_{10}$-oxo alcohol ethoxylate with a degree of ethoxylation of about 4, 4 parts by weight of a commercial alkylcarboxylic acid mixture as solubilizer, 7 parts by weight of sodium gluconate to break down the water hardness and 25 parts by weight of water
was used to remove deposits of calcium phosphate, calcium oxalate, protein and ash. It was possible to remove the deposits without difficulty.

Example 14
Highly alkaline cleaner formulation for breweries
A mixture of 40 parts by weight of 50% by weight potassium hydroxide solution, 20 parts by weight of a 30% by weight aqueous solution of α-D,L-alanine-N,N-diacetic acid trisodium salt from Example No. 2, 3 parts by weight of a $C_{10}$-oxo alcohol ethoxylate with a degree of ethoxylation of about 3, 3 parts by weight of a commercial alkylcarboxylic acid mixture as solubilizer and 34 parts by weight of water was used to remove deposits of calcium oxalate, hop resins and protein. It was possible to remove the deposits without difficulty.

We claim:

1. A process for preparing glycine-N,N-diacetic acid derivatives of the general formula I

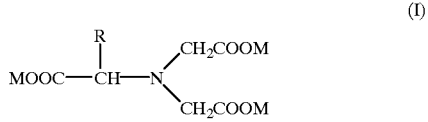

(I)

in which

R is $C_1$- to $C_{30}$-alkyl or $C_2$- to $C_{30}$-alkenyl, which can additionally carry as substituents up to 5 hydroxyl groups, formyl groups, $C_1$- to $C_4$-alkoxy groups, phenoxy groups or $C_1$- to $C_4$-alkoxycarbonyl groups and be interrupted by up to 5 non-adjacent oxygen atoms, alkoxylate groups of the formula —$(CH_2)_k$—O—$(A^1O)_m$—$(A^2O)_n$—Y, in which $A^1$ and $A^2$ are, independently of one another, 1,2-alkylene groups with 2 to 4 carbon atoms, Y is hydrogen, $C_1$- to $C_{12}$-alkyl, phenyl or $C_1$- to $C_4$-alkoxycarbonyl, and k is 1, 2 or 3, and m and n are each numbers from 0 to 50, where the total of m+n must be at least 4, phenylalkyl groups with 1 to 20 carbon atoms in the alkyl, a five- or six-membered unsaturated or saturated heterocyclic ring with up to three heteroatoms selected from the group consisting of nitrogen, oxygen and sulfur, which can additionally be benzo-fused, where all the phenyl nuclei and heterocyclic rings mentioned in the meanings of R can additionally also carry as substituents up to three $C_1$- to $C_4$-alkyl groups, hydroxyl groups, carboxyl groups, sulfo groups or $C_1$- to $C_4$-alkoxycarbonyl groups, or a radical of the formula

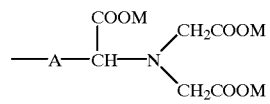

where A is a $C_1$- to $C_{12}$-alkylene bridge or a chemical bond, and

M is hydrogen, alkali metal, alkaline earth metal, ammonium or substituted ammonium in the appropriate stoichiometric amounts, which comprises reacting A) appropriate 2-substituted glycines or 2-substituted glycinonitriles or doubled glycines of the formula

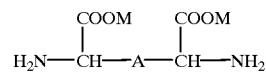

or doubled glycinonitriles of the formula

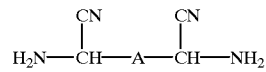

with formaldehyde and hydrogen cyanide or

B) iminodiacetic acid or iminodiacetonitriles with appropriate monoaldehydes or dialdehydes of the formula OHC—A—CHO and hydrogen cyanide or alkali metal cyanide and subsequently hydrolyzing nitrile groups which are still present to carboxyl groups.

2. The process of claim 1, wherein the use also of additional acid in embodiment A is dispensed with.

3. The process of claim 1, wherein embodiment B is carried out in the pH range from 0 to 11.

4. A glycine-N,N-diacetonitrile or glycinonitrile-N,N-diacetonitrile which is substituted by the radical R in position 2, in which R is is $C_1$- to $C_{30}$-alkyl or $C_2$- to $C_{30}$-alkenyl, which can additionally carry as substituents up to 5 hydroxyl groups, formyl groups, $C_1$- to $C_4$-alkoxy groups, phenoxy groups or $C_1$- to $C_4$-alkoxycarbonyl groups and be interrupted by up to 5 non-adjacent oxygen atoms, alkoxylate groups of the formula —$(CH_2)_k$—O—$(A^1O)_m$—$(A^2O)_n$—Y, in which $A^1$ and $A^2$ are, independently of one another, 1,2-alkylene groups with 2 to 4 carbon atoms, Y is hydrogen, $C_1$- to $C_{12}$-alkyl, phenyl or $C_1$- to $C_4$-alkoxycarbonyl, and k is 1, 2 or 3, and m and n are each numbers from 0 to 50, where the total of m+n must be at least 4, phenylalkyl groups with 1 to 20 carbon atoms in the alkyl, a five- or six-membered unsaturated or saturated heterocyclic ring with up to three heteroatoms selected from the group consisting of nitrogen, oxygen and sulfur, which can additionally be benzo-based, where all the phenyl nuclei and heterocyclic rings mentioned in the meanings of R can additionally also carry as substituents up to three $C_1$- to $C_4$-alkyl groups, hydroxyl groups, carboxyl groups, sulfo groups or $C_1$- to $C_4$-alkoxycarbonyl groups, and a doubled glycine-N,N- diacetonitrile and doubled glycinonitrile-N,N-diacetonitrile of the formula
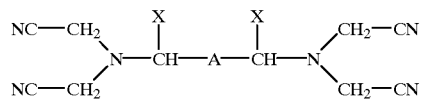
where X is a carboxylic acid or a nitrile functionality, as intermediates.